United States Patent
Butterfield

(10) Patent No.: US 9,205,187 B2
(45) Date of Patent: *Dec. 8, 2015

(54) MANAGING A FLUID FLOW

(75) Inventor: Robert Dwaine Butterfield, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 641 days.

This patent is subject to a terminal disclaimer.

(21) Appl. No.: 13/494,874

(22) Filed: Jun. 12, 2012

(65) Prior Publication Data

US 2013/0331789 A1      Dec. 12, 2013

(51) Int. Cl.
| | |
|---|---|
| *A61M 1/00* | (2006.01) |
| *A61M 5/00* | (2006.01) |
| *A61M 5/14* | (2006.01) |
| *A61M 5/168* | (2006.01) |
| *A61M 5/40* | (2006.01) |
| *A61M 39/28* | (2006.01) |

(52) U.S. Cl.
CPC ........... *A61M 5/1408* (2013.01); *A61M 5/1684* (2013.01); *A61M 5/16827* (2013.01); *A61M 5/40* (2013.01); *A61M 39/284* (2013.01)

(58) Field of Classification Search
CPC ............ A61M 39/284; A61M 5/1408; A61M 5/16827; A61M 5/1684; A61M 5/40

USPC .......................................................... 604/151
See application file for complete search history.

(56) References Cited

U.S. PATENT DOCUMENTS

| | | | |
|---|---|---|---|
| 4,533,347 A | 8/1985 | Deckert | |
| 4,946,439 A | 8/1990 | Eggers | |
| 5,032,112 A | 7/1991 | Fairchild et al. | |
| 6,554,806 B2 | 4/2003 | Butterfield et al. | |
| 7,302,960 B2 * | 12/2007 | Patzer | ............................ 137/12 |
| 8,545,446 B1 | 10/2013 | Butterfield | |

* cited by examiner

*Primary Examiner* — Jason Flick
(74) *Attorney, Agent, or Firm* — Fred C. Hernandez; Mintz Levin Cohn Ferris Glovsky and Popeo, P.C.

(57) ABSTRACT

A device including: a tubing clamp having a clamping mechanism holding closed a first fluid line while a second fluid flows along a second fluid line from a second container, the first fluid line delivers a flow of a first fluid; and a vacuum activated catch retainably coupled with the tubing clamp and coupled with the second fluid line, the vacuum activated catch including: a movable element coupled with the tubing clamp and configured for changing from a first shape to a second shape upon receipt of a deforming pressure, wherein when the movable element is in the first shape, the vacuum activated catch retains the tubing clamp in a closed position, and when the movable element is in the second shape, the vacuum activated catch releases the tubing clamp into an open position, thereby allowing the flow of the first fluid to commence within the first fluid line.

12 Claims, 12 Drawing Sheets

500

```
RECEIVES A FLUID FLOW, THE RECEIVING OCCURRING AT A DRIP FORMING ORIFICE
OF A DRIP CHAMBER, THE FLUID FLOW OCCURRING AT A FIRST RATE IN A FIRST
DIRECTION
505
```
↓
```
RESISTS THE FLUID FLOW BY THE DRIP FORMING ORIFICE
510
```
↓
```
STOPS THE FLUID FLOW BY A CHECK VALVE, THE CHECK VALVE COUPLED WITH
AND POSITIONED BETWEEN A SPIKE AND A DRIP FORMING ORIFICE, THE SPIKE
BEING INTEGRALLY COUPLED WITH A FIRST END OF THE DRIP CHAMBER
515
```
↓
```
DAMPS AT LEAST A PORTION OF AN EFFECT OF A PRESSURE PULSE FORMED BY AN
INFUSION PUMP, THE INFUSION PUMP BEING FLUIDLY COUPLED WITH THE DRIP
CHAMBER, THE DAMPING INCLUDING, IN RESPONSE TO RECEIVING THE PRESSURE
PULSE FROM THE INFUSION PUMP, ELASTICALLY EXPANDING AT AN AIR HOLDING
PORTION AND AT LEAST A PORTION OF AN ENCLOSING WALL OF THE DRIP
CHAMBER, THEREBY THE DAMPING AT LEAST A PORTION OF THE EFFECT OF THE
PRESSURE PULSE
520
```
↓
```
DAMPS AT LEAST A PORTION OF AN EFFECT OF A PRESSURE PULSE FORMED BY AN
INFUSION PUMP, THE INFUSION PUMP BEING FLUIDLY COUPLED WITH THE DRIP
CHAMBER VIA A TUBING, WHEREIN THE TUBING ELASTICALLY EXPANDS IN
RESPONSE TO RECEIVING OF THE PRESSURE PULSE FROM THE INFUSION PUMP
AND PROVIDES A RESISTANCE WITHIN TO MOVEMENT OF THE FLUID FLOW
THERE THROUGH
525
```
↓
```
RELEASES A VOLUME OF THE FLUID FLOW AT THE CHECK VALVE, THE RELEASING
INCLUDING: RECEIVING A CHECK VALVE OPENING TRIGGER; AND IN RESPONSE TO
THE RECEIVING THE CHECK VALVE OPENING TRIGGER, OPENING THE CHECK VALVE
530
```

PROVIDES A TUBING CLAMP, WHEREIN THE TUBING CLAMP INCLUDES: A CLAMPING MECHANISM CONFIGURED FOR HOLDING CLOSED A FIRST FLUID LINE WHILE A SECOND FLUID FLOWS ALONG A SECOND FLUID LINE FROM A SECOND CONTAINER, THE FIRST FLUID LINE CONFIGURED FOR DELIVERING A FLOW OF A FIRST FLUID
1005

↓

COUPLES A VACUUM ACTIVATED CATCH WITH THE TUBING CLAMP, WHEREIN THE VACUUM ACTIVATED CATCH INCLUDES: A MOVABLE ELEMENT COUPLED WITH THE TUBING CLAMP AND CONFIGURED FOR CHANGING FROM A FIRST SHAPE TO A SECOND SHAPE UPON RECEIPT OF A DEFORMING PRESSURE, WHEREIN WHEN THE MOVABLE ELEMENT IS IN THE FIRST SHAPE, THE VACUUM ACTIVATED CATCH RETAINS THE TUBING CLAMP IN A CLOSED POSITION, AND WHEN THE MOVABLE ELEMENT IS IN THE SECOND SHAPE, THE VACUUM ACTIVATED CATCH RELEASES THE TUBING CLAMP INTO AN OPEN POSITION, THEREBY ALLOWING THE FLOW OF THE FIRST FLUID TO COMMENCE WITHIN THE FIRST FLUID LINE
1010

↓

DISPOSES AT LEAST ONE LATCHING ELEMENT ON THE MOVABLE ELEMENT, SUCH THAT THE MOVABLE ELEMENT IS ENABLED TO SECURE THE TUBING CLAMP IN A CLOSED POSITION
1015

FIG. 10

MANAGING A FLUID FLOW

CROSS-REFERENCE TO RELATED U.S. PATENT APPLICATIONS

This application is related to U.S. patent application Ser. No. 13/494,816, filed on Jun. 12, 2012, entitled "DRIP CHAMBER", and assigned to the assignee of the present application. To the extent not repeated herein, the contents of this related patent application are hereby incorporated herein by reference.

This application is related to U.S. patent application Ser. No. 13/494,900, filed on Jun. 12, 2012, entitled "FLUID MECHANICAL DEVICE FOR IMPROVED SECONDARY MODE IV DELIVERY", and assigned to the assignee of the present application. To the extent not repeated herein, the contents of this related patent application are hereby incorporated herein by reference.

FIELD

Embodiments relate generally to the field of medical infusion therapy. More particularly, embodiments relate to intravenous therapy.

BACKGROUND

In general, intravenous therapy is used to administer substances directly into a vein of a patient. Many tubing systems used in administration of intravenous or parenteral therapy employ a drip chamber. The drip chamber prevents air from entering the blood stream, causing air embolism. The drip chamber also allows for a flow rate of the administered substance to be estimated. Further, the drip chamber offers a means to vent closed containers, such as bottles, thereby permitting filtered air to replace the fluid removed and thus avoiding the formation of a vacuum that would inhibit flow. Some substances that may be infused intravenously include volume expanders, blood-based products, blood substitutes, buffer solutions and medications.

Typically, the traditional IV infusion setup includes a pre-filled, sterile container (glass bottle, plastic bottle or plastic bag) of fluid(s) with a tubular port that allows the attachment of an IV set's drip chamber "spike". The IV set's drip chamber includes: a drip chamber orifice that allows the fluid to form drops of an approximate volume at slow flow rates, making it easy to see the flow rate (and also to avoid the entrainment of air bubbles in the tubing); a long sterile tube with a variable restriction clamp to regulate or stop the flow of fluids; a connector to attach to the vascular access device (VAD); connectors and a one-way check valve to allow "piggybacking" (Secondary mode infusion setup) of another infusion set onto the same line, e.g., for adding a dose of antibiotics to a continuous fluid drip. Further, the addition of an infusion pump to the IV infusion setup allows for control over the flow rate and total fluid volume delivered to a patient.

In certain cases, where a change in flow rate and a total volume delivered would not have serious consequences, flow is produced by elevating the container above the patient and employing gravity pressure in concert with manual adjustment of a clamp and visual monitoring of the rate of drop formation in the drip chamber to regulate the flow rate. Limitations exist with regards the administration of multiple substances using such a gravity mode intravenous therapy setup.

DESCRIPTION OF THE DRAWINGS

FIG. 5 shows a flow diagram of an example method for managing a flow of fluid within a flow control system, in accordance an embodiment.

FIG. 10 shows a flow diagram of an example method for manufacturing a device, in accordance with an embodiment.

The drawings referred to in this description should not be understood as being drawn to scale unless specifically noted.

DESCRIPTION OF EMBODIMENTS

Reference will now be made in detail to various embodiments, examples of which are illustrated in the accompanying drawings. While the subject matter will be described in conjunction with these embodiments, it will be understood that they are not intended to limit the subject matter to these embodiments. On the contrary, the subject matter described herein is intended to cover alternatives, modifications and equivalents, which may be included within the spirit and scope. Furthermore, in the following description, numerous specific details are set forth in order to provide a thorough understanding of the subject matter. However, some embodiments may be practiced without these specific details. In other instances, well-known structures and components have not been described in detail as not to unnecessarily obscure aspects of the subject matter.

Section One

Pressure Wave Damping Drip Chamber

Overview of Discussion

Herein, various embodiments of a drip chamber, a fluid control system and methods for controlling the flow of fluid are described. The description begins with a brief general discussion of a traditional flow control system and drip chamber. This general discussion provides a framework of understanding for more particularized descriptions of features and concepts of operation associated with one or more embodiments of the described fluid control technology.

Flow Control Systems with Respect to Drip Chambers

As discussed herein, traditional flow control systems are used to apply intravenous or intravascular (IV) therapy. IV therapy is the administration of substances directly into a vascular system of a patient. Many systems of administration of IV therapy use a "drip chamber". The drip chamber, in general, prevents air from entering the IV tubing and ultimately the blood stream (causing air embolism) and allows for an estimate of a flow rate of the medication administered.

Figure 1:
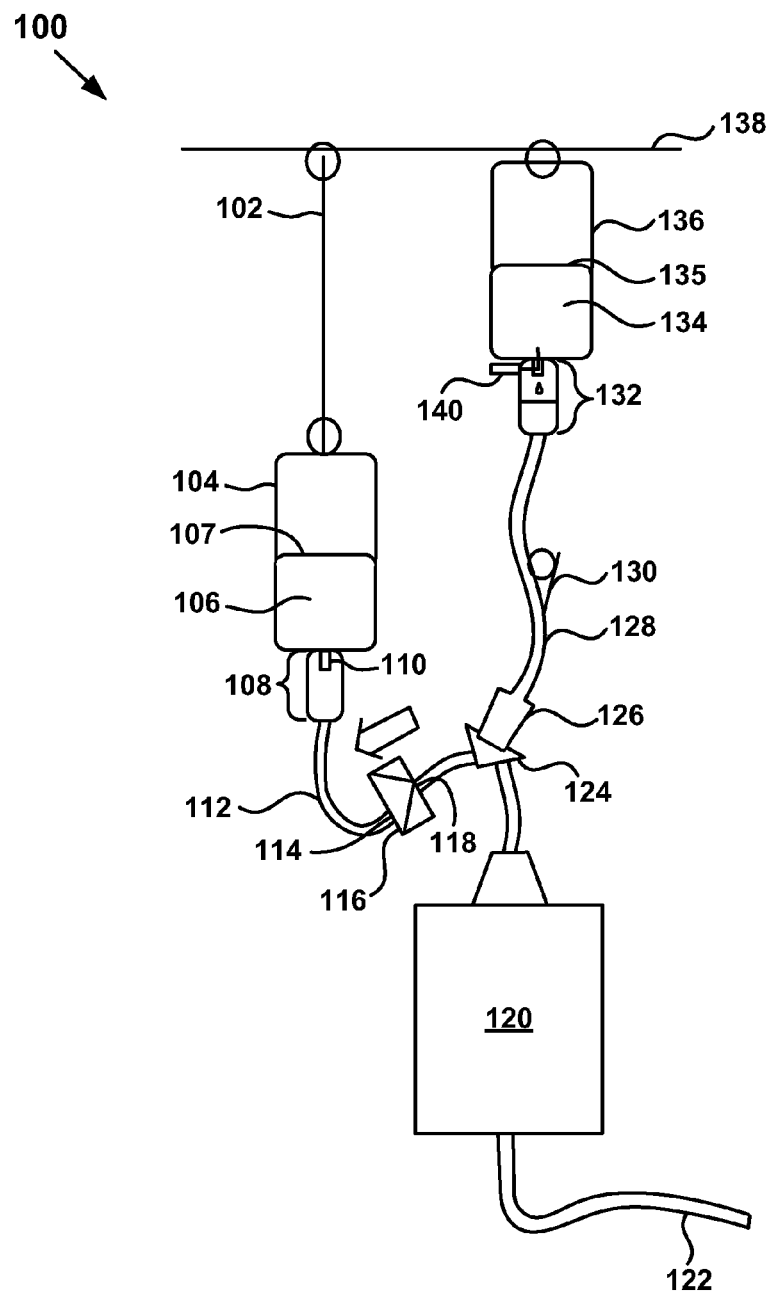
FIG. 1 is an example of a traditional Secondary mode infusion setup.

Referring now to FIG. 1, an example of a traditional Secondary mode infusion setup 100 is shown. Traditional Secondary mode infusion setup 100 includes a Primary container 104 coupled with a Primary drip chamber 108, and a Secondary container 136 (positioned at a location higher than the Primary container 104) coupled with a Secondary drip chamber 132. The Primary container hangs from the hanger 102, while the Secondary container 136 hangs from the same line 138 from which the hanger 102 is attached. The Primary drip chamber 108 is coupled with a Primary fluid line 112, wherein the Primary fluid line 112 runs to a pump 120. In between the Primary drip chamber 108 and the pump 120, a check valve 116 is coupled with the Primary fluid line 112. Further, the Secondary drip chamber 132 is coupled with a Secondary fluid line 128, wherein the Secondary fluid line 128 also runs to the pump 120. In between the Secondary drip chamber 132 and the pump 120, a male luer 126 and needle-free valve connection 124 is coupled with the Secondary fluid line 128. On the downstream side, or patient-side portion, of the administration set of the pump 120 is a vascular access device (aka catheter, e.g. IV fluid line 122) or interconnecting plumbing such as an extension set or a needlefree valve.

When the Secondary fluid level 135 in the Secondary container 136 is at a level above the Primary fluid level 107, a hydrostatic pressure differential is created across the check valve 116 causing it to close, thereby preventing flow of the Primary fluid 106 from the Primary container 104 to the pump 120 and significantly, preventing reverse flow of the Secondary fluid 134 into the Primary container 104. However, when the Secondary fluid level 135 decreases as fluid is withdrawn and/or if the Secondary container 136 is lowered such that the Secondary fluid level 134 is at about the same height as the Primary fluid level 107, the pressures directed at the inlet 114 and the outlet 118 of the check valve 116 approach equilibrium. Ideally, when the Primary side pressure on the check valve 116 becomes just slightly greater than the Secondary side pressure on the check valve 116, the pump 120 will draw fluid solely from the Primary container 104.

Even if the Secondary fluid level 135 is higher than the Primary fluid level 107, if the pump flow rate is in the range of 250 to 1000 milliliters per hour, there may be pressure loss through a restriction in the flow path of the Secondary container 136, such as due to the connection between the male luer 126 and the needle-free valve connection 124. Flow through a restriction (Of note, there may be multiple restrictive elements such as a vent in the drip chamber which has become wetted, thereby increasing its resistance to flow.) causes a pressure loss, thereby reducing the pressure applied on the check valve 116 from the Secondary side. When there is just a slightly positive pressure across the check valve 116 from the Primary side, the check valve 116 will open, thereby allowing flow from the Primary container 104 to occur intermittently with each pulse of flow aspirated by the pump. Thus, there may be concurrent flow from both the Primary and Secondary containers, 104 and 136, respectively, in some varying proportion dependent on the flow rate, the restriction and the degree of pulsatility of the pump's intake flow pattern.

When the Secondary fluid level 135 has lowered sufficiently in the Secondary container 136, the pressure of the Primary fluid 106 will remain consistently slightly higher than the pressure of the Secondary fluid 134. The check valve 116 is continuously open allowing all the fluid to preferentially be drawn from the Primary container 104, while the Secondary fluid level 135 in the Secondary container 136 will remain fairly constant. Note that at this point, since there is no flow coming from the Secondary container 136, no pressure pulses are being produced via the Secondary restriction, so the check valve 116 is held open by the differential pressure between the Secondary container 136 and the Primary container 104, only.

In the delivery of chemotherapy, clinicians frequently use the traditional Secondary mode infusion setup 100. This is in part owing to its convenience and safety in the handling and transport of the medication and is in part due to the frequent need to infuse pre and post medication fluids via the same IV catheter. While using the traditional Secondary mode infusion setup 100 within an oncology framework, several issues and problems become apparent. Firstly, larger and taller bags and bottles (containers) are used to hold a large volume of medication. Secondly, much higher flow rates than the traditional Secondary mode infusion setup 100 was originally designed for are used. Thirdly, the use of some needle-less (a.k.a. needle-free) valve connectors may present somewhat higher flow restrictions in the Secondary pathway than the large bore metal needle/rubber port used when the traditional Secondary mode infusion setup 100 was developed. Fourthly, the length of hangers for lowering the Primary container 104 may not be adequate to lower the Primary container sufficiently to assure adequate pressure differential in these demanding applications.

As the Secondary fluid 134 finishes delivery, the taller Secondary container(s) 136 together with inadequate hanger length means that the elevation of the Secondary fluid 134 relative to the Primary fluid level 107 will be lower than with smaller Secondary container(s). Without an adequate pressure difference of the Secondary side over the Primary side, the Primary fluid 106 can begin flowing prematurely before the Secondary fluid 134 is completely delivered, due to the normal action of the check valve 116. This may result in delayed delivery completion of the Secondary fluid 134, since for each drop of the Primary fluid 106 delivered, a drop of Secondary fluid 134 is NOT delivered. Thus, some amount of the Primary fluid 106 replaces some amount of the Secondary fluid 134 as its level lowers, thereby causing the inadvertent delay in the delivery completion of the Secondary fluid 134. Further, the check valve 116 located along the Primary fluid line 112 may transiently open prior to completion of the delivery of Secondary fluid 134 due to pump-flow-induced transient drops in pressure, thereby producing a condition of concurrent flow in varying proportion from both the Primary and Secondary containers, 104 and 136, respectively.

The intake flow from pumps is not entirely steady. In fact, in many pump designs, the pump 120 draws fluid in at several times the mean outflow rate. When these rapid flows occur, they cause a pressure loss through any restriction in the Secondary pathway such as at a needle-free valve connection 124 or a blocked intake air vent 140. These transient pressure drops allow the check valve 116 to open very briefly, and then close. Thus, even if there was a suitable head height difference between the Secondary fluid level 135 and the Primary fluid level 107, there may still be inadequate pressure within the Primary fluid line 112 to prevent inadvertent partial flow from the Primary container 104 while fluid remains to be delivered in the Secondary container 136. (In other words, and briefly, the restriction of the Secondary fluid line 128 is too high and the pulsation of the intake of the pump 120 is too abrupt, causing the inadvertent partial flow from the Primary container 104 while fluid remains to be delivered in the Secondary container 136.) For oncology and other patients who similarly require a particular volume of medication to be administered within a precisely defined period of time, the delayed delivery completion of the Secondary fluid 134 from the Secondary container 136 may result in complications in scheduling subsequent therapy and other clinical management difficulties for the hospital.

Embodiments incorporate a check valve placed uniquely within a drip chamber of a Primary delivery set, thereby overcoming many of the problems besetting the traditional infusion setup 100. In one embodiment, the drip chamber is used with IV therapy. However, while embodiments are described within the context of IV therapy, it should be understood that the concepts described herein may be applied to a device/integration within equipment other than for use in IV therapy.

Embodiments allow for taller containers, higher flow rates, Secondary path connections having less than ideal low resistance and pumps having less than ideal smooth intake flow to be used during IV therapy, while still preventing flow through the Primary fluid line when the Secondary container is nearly empty (i.e. substantially empty). As noted earlier, when elevations of Primary and Secondary fluids are about equal, the check valve no longer is held closed and thus allows the Primary fluid to flow (intended). In practice, the Secondary level may have to be just a small amount lower than the Primary fluid due to the design of some check valves which requires a so called 'cracking pressure' to open. This is typically no more than one inch of water pressure (elevation). Embodiments provide for no flow coming from the Secondary container. If flow did come from the Secondary container, then the reduced Secondary pressure would quickly reopen the check valve, thereby drawing fluid totally from the Primary container. More specifically, embodiments mitigate the effect of pressure pulses that cause the check valve to open intermittently before the Secondary fluid has been completely delivered.

Moreover, in one embodiment, by having a (one-way) check valve placed above the drip forming orifice and the pocket of air within the drip chamber (along with a controlled restriction in the drip chamber orifice), wherein the walls of the drip chamber provide a certain amount of elasticity, the likelihood that the pressure pulses from the infusion pump would cause an unwanted Primary fluid to replace desired Secondary fluid prior to the delivery of the Secondary fluid is significantly reduced. By placement of a check valve more remote (further upstream) from its typical placement near the connecting port, the inherent elasticity of the Primary tubing together with its own resistance therein to a movement of fluid there through provide an additional source of damping of the effects of the pressure wave of the infusion pump. The walls of the drip chamber itself, along with the fluid resistance and fluid inertance within the drip forming orifice, damp the negative pressure created by the pressure pulses from the infusion pump. By damping the negative pressure pulses created by the infusion pump's intake flow pattern, the now steady reverse pressure across the check valve prevents the Primary fluid from moving through the check valve.

In one embodiment, the one-way check valve includes a bypass mechanism. The bypass mechanism allows the one-way check valve, in response to a signal, to open to allow Primary fluid to move through the one-way check valve in a direction that is reverse to the direction of the current fluid flow from the container. This bypass mechanism enables practitioners to expel excess IV fluid from the drip chamber back into the container by inverting the drip chamber and gently squeezing it. This allows adjustment of the amount of fluid in the drip chamber to permit visualization of drops. It should be appreciated that alternate embodiments may include "bypass" mechanisms, other than the bypass mechanism described herein, that enable the release of fluid through a fluid line. For example, but not limited to such, a channel parallel to the check valve may be opened by a deformation of the fluid pathway and/or by an activation of a lever (or similar device).

Thus, embodiments improve the accuracy of the Secondary Mode delivery of substances by minimizing the unintended flow from a Primary container while the Secondary fluid remains to be delivered. For example, for time-critical Secondary applications, such as chemotherapy, where flows are high (>300 ml/h), pressure loss through the Secondary pathway is exacerbated by the pulsatile intake flow of many pumps. Embodiments markedly minimize the exposure of the check valve to these pulsatile pressures, thereby reducing unintended check valve opening with attendant flow from the Primary container prior to completion of the Secondary fluid administration.

Additionally, embodiments reduce the cost of the Primary set by integrating components and reducing labor during its manufacture. Currently, one check valve is used in a significant percentage of Primary sets built. Assembly of these check valves into the finished delivery set adds steps and points for possible failure. By integrating the check valve within the drip chamber, manufacturing steps are eliminated, resources are saved and reliability can be improved.

Figure 2:
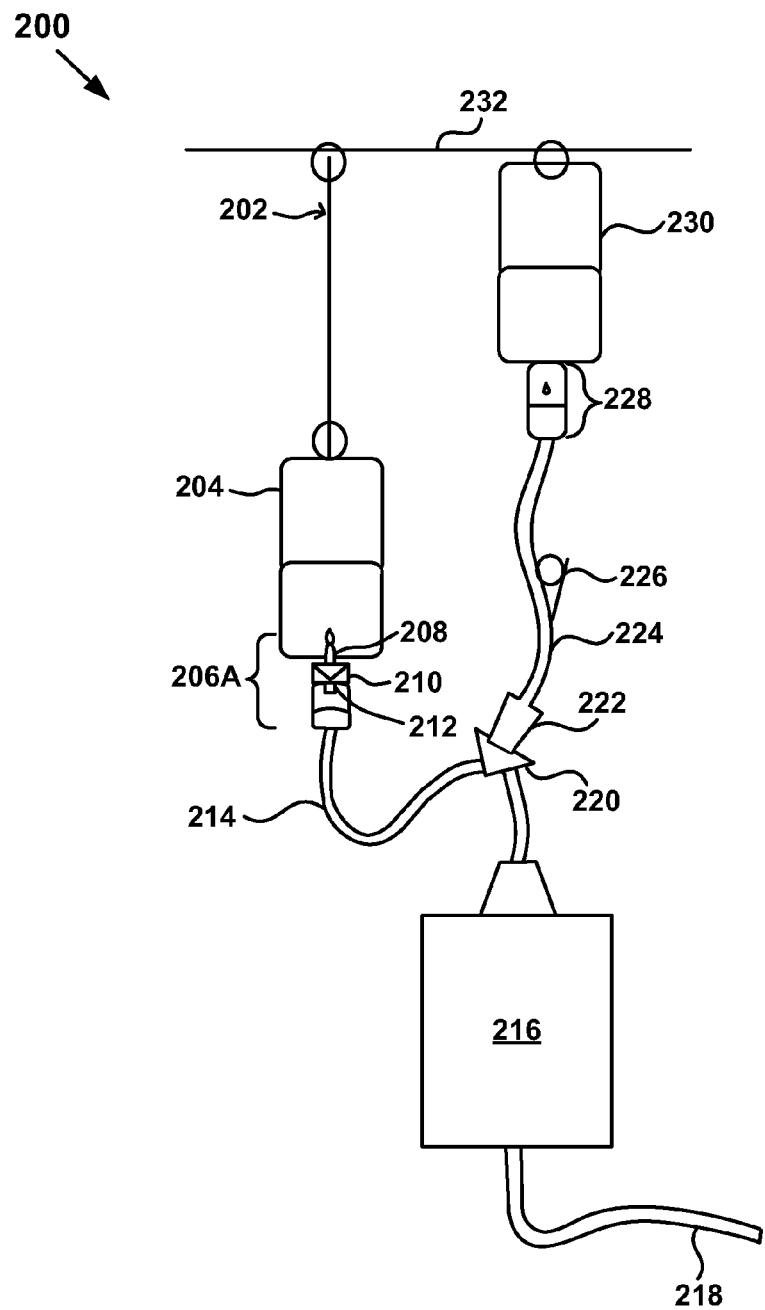
FIG. 2 shows an example Secondary mode infusion setup, including a drip chamber, in accordance with an embodiment.

The following discussion will focus on example structures and example operations, in accordance with embodiments. For clarity and ease of explanation of an example first drip chamber 206A (of FIG. 2), FIG. 2 shows a Secondary mode infusion setup 200 (hereinafter, "infusion setup 200"), in accordance with an embodiment. The drip chamber 206B of FIG. 3 and the drip chamber 206C of FIG. 4 are enlarged views of first drip chamber 206A of FIG. 2, in accordance with an embodiment. The infusion setup 200 shows the first container 204 (supported by hanger 202) and the second container 230 hanging directly from the line 232. Further, the first and second containers, 204 and 230, respectively, in various embodiments, may be used in a device/integration within equipment other than for use in IV therapy.

In one embodiment, the first container 204 is a Primary container, the first fluid line 214 is a Primary fluid line, the first fluid 234 is a Primary fluid, the second container 230 is a Secondary container, the second drip chamber 228 is a Secondary drip chamber, the second fluid line 224 is a Secondary fluid line, the second fluid 236 is a Secondary fluid, the first fluid flow is a Primary fluid flow, and the second fluid flow is a Secondary fluid flow. Thus, the descriptions herein, with regards to FIGS. 1-6, using the terms "first" and "second" may be associated with the delivery of Secondary medications (as is commonly known in the art), in one embodiment.

The first drip chamber 206A is coupled with and between the first container 204 and the infusion pump 216. The first fluid line 214 couples the first drip chamber 206A with the infusion pump 216. The first drip chamber 206A includes a spike 208, a drip forming orifice 212 (providing a controlled restriction or "fluid resistance") and a check valve 210 coupled with and between the spike 208 and the drip forming orifice 212.

As part of the infusion setup 200, a second drip chamber 228 is shown coupled with and between the second container 230 and the infusion pump 216. Of note, the second drip chamber 228 does not include all of the features of the first drip chamber 206A. The second fluid line 224 couples the second drip chamber 228 with the infusion pump 216. In one embodiment, attached to the second fluid line 224, between the second drip chamber 228 and the infusion pump 216, are a roller clamp 226, a male luer 222 and a needle-free valve connection 220. It should be appreciated that the roller clamp 226, the male luer 222 and the needle-free valve connection 220 may be those that are commonly known in the art. A patient IV fluid line 218 is coupled with the infusion pump 216 and transports the fluid drawn from the first and/or second containers, 204 and 230, respectively, to the patient.

Figure 3:
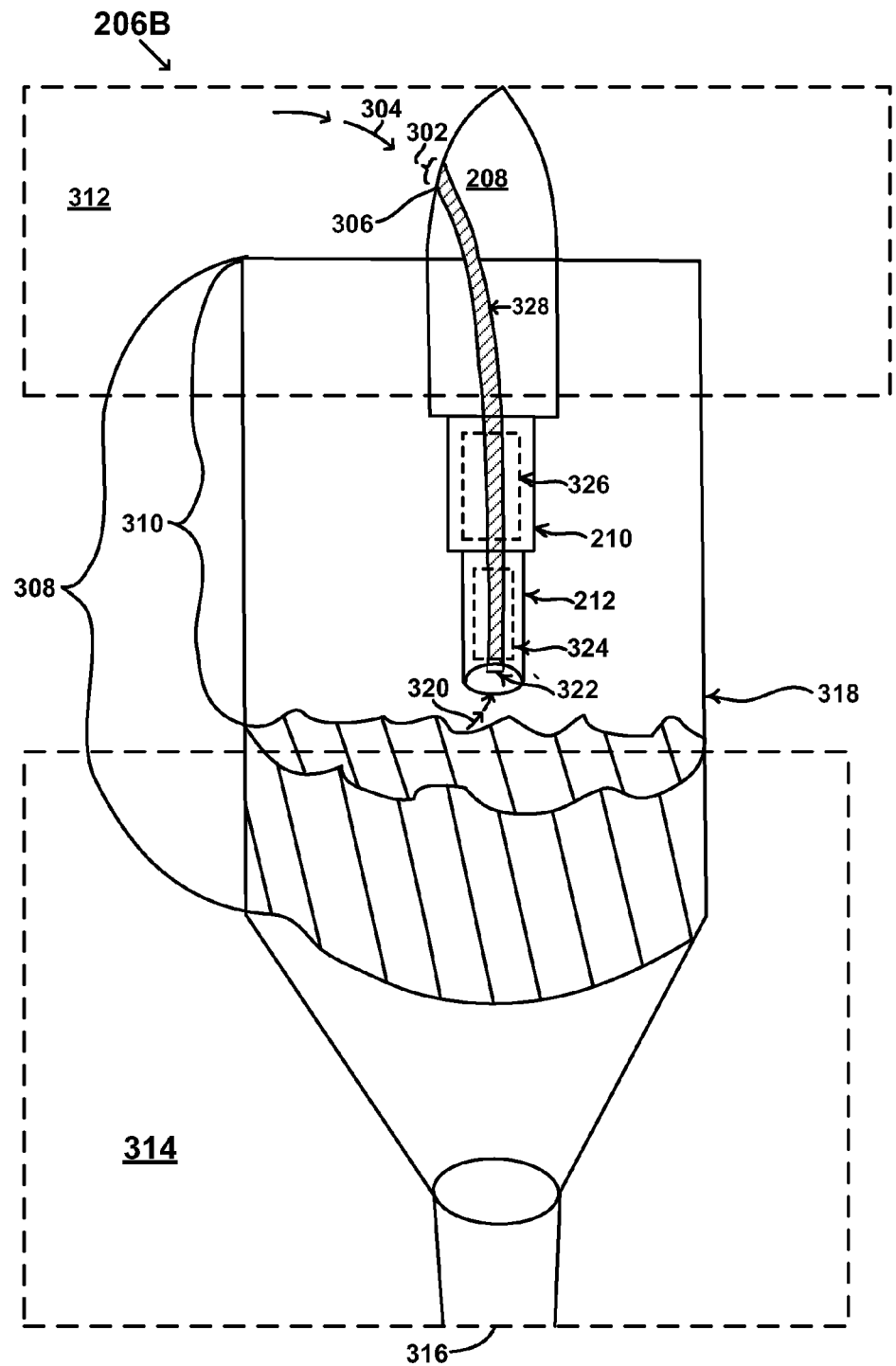
FIG. 3 shows a cross-sectional view of the example drip chamber of FIG. 2, in accordance with an embodiment.
Figure 4:
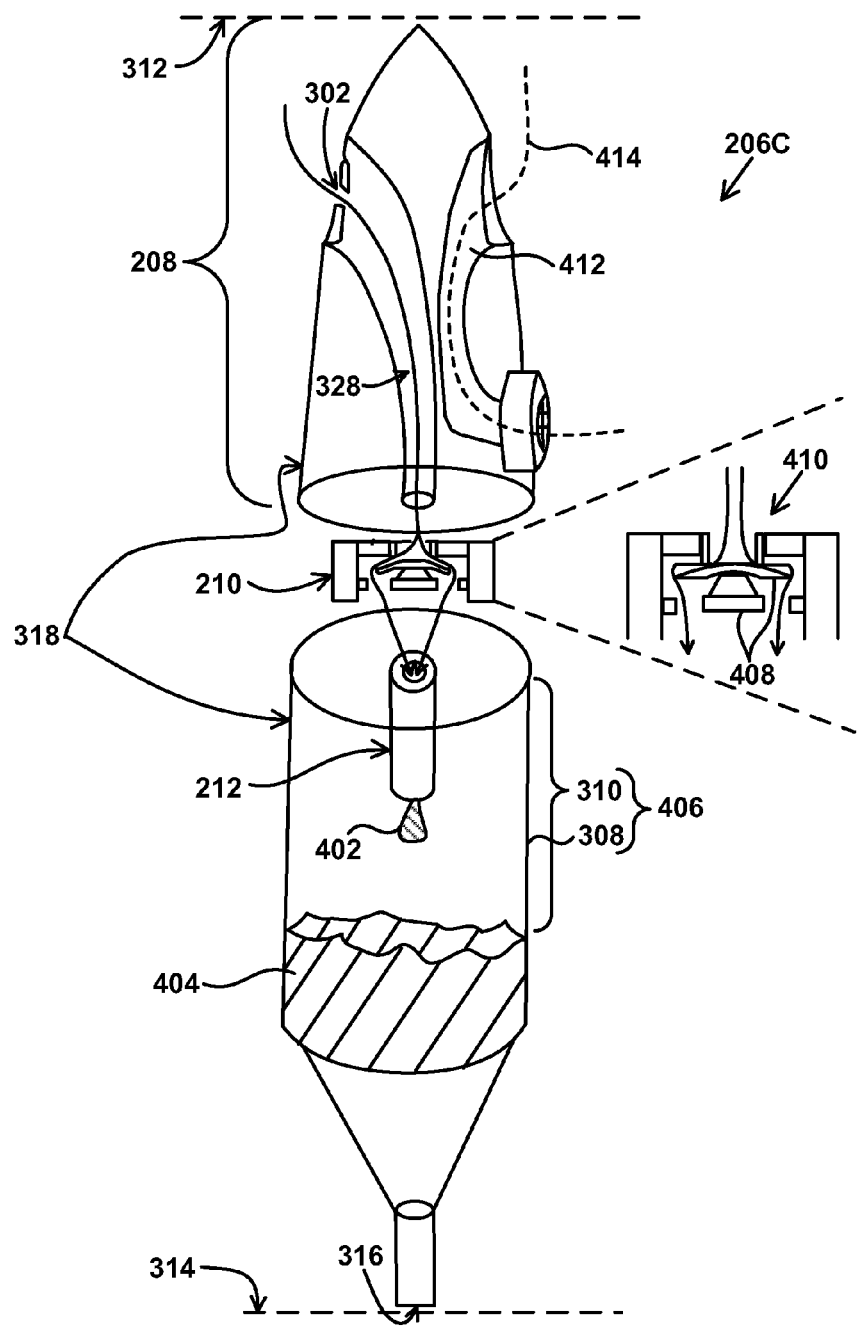
FIG. 4 shows a cross-sectional view of the example drip chamber of FIG. 2, in accordance with an embodiment.

The drip chamber 206B is shown as a block diagram in FIG. 3, in accordance with an embodiment. The drip chamber 206B is an enlargement of the first drip chamber 206A of FIG. 2, the details of which will be discussed herein. FIG. 4 shows a drip chamber 206C, a cross-sectional view of the first drip chamber 206A (FIG. 2) and drip chamber 206B (FIG. 3), in accordance with an embodiment, the details of which will be discussed herein.

Referring now to FIG. 3, in one embodiment, the drip chamber 206B includes: a first end 312; a second end 314; a spike 208; a drip forming orifice 212 (providing a controlled restriction to flow); a check valve 210; and an enclosing wall 318. The first end 312 includes an inlet 302. The second end 314 includes an outlet 316. The spike 208 is integrally coupled with the first end 312. More specifically, the spike 208 is coupled with the rest of the body of the drip chamber 206B such that the outer wall of the spike 208 is included as a portion of the "housing" of the drip chamber 206B at the first end 312.

In different embodiments, portions of the first end 312 include different components, and portions of the second end 314 include different components. For example, but not limited to such, in one embodiment, the first end 312 of the drip chamber 206B includes the spike 208 and the check valve 210. However, in another embodiment, the first end 312 includes just the spike 208. Similarly, the second end 314 of the drip chamber 206B includes the outlet 316, the air holding portion 310 (discussed later) and the drip forming orifice 212, in one embodiment. However, in another embodiment, the second end 314 of the drip chamber 206B includes the outlet 316, the air holding portion 310, the drip forming orifice 212 and the check valve 210.

In one embodiment, the drip forming orifice 212 is coupled with the spike 208, with the check valve 210 disposed there between. An interior flow passage 328 runs through and between the spike 208, check valve 210 and drip forming orifice 212 (which also, in one embodiment, provides a path that includes a flow restriction). The first end 306 of the interior flow passage 328 is positioned at the inlet 302 of the drip chamber 206B. The second end 322 of the interior flow passage 328 is positioned at the intake side of the check valve 210. Connected to the outlet of the check valve 210 is the lower section of the interior flow passage 328, which also connects to the drip forming orifice 212. Further, the enclosing wall 318, which is coupled with the first end 312 and the second end 314, houses within the spike 208, the check valve 210 and the drip forming orifice 212.

In one embodiment, the check valve 210 is a one-way check valve. Again, of note, the check-valve is typically one-way by design. The one-way check valve allows a fluid to flow in a second direction 304 within the interior flow passage 328, while stopping a fluid from flowing in a first direction 320 within the interior flow passage 328. Referring now to FIGS. 2 and 3, in one example, the fluid flowing in the second direction 304 is the first fluid 234 from the first container 204, and the fluid attempting to flow in the first direction 320 is the second fluid 236 from the second container 230. The fluid flowing in the second direction 304 is flowing in an opposite direction as the fluid attempting to flow in the first direction 320. Thus, the check valve 210 allows the first fluid 234 to flow down to the first fluid line 214 to the infusion pump 216, while stopping any fluid from flowing up through the check valve 210 and into the first container 204. This fluid that is stopped may be the first fluid 234 itself that has already traveled past the drip forming orifice 212, and/or it may be second fluid 236 having been drawn into the drip chamber 206B.

Referring still to FIGS. 2 and 3, in one embodiment, the drip chamber 206B includes a pressure damping elastic component. The pressure damping elastic component includes an air holding portion 310 of the drip chamber 206B and at least a portion 308 of the enclosing wall 318 that is elastic. It should be appreciated that the at least a portion 308 of the enclosing wall 318 that is elastic may be all of the enclosing wall 318, or a portion less than an entirety of the enclosing wall 318. The air holding portion 310 of the drip chamber 206B holds air. The air holding portion 310 and the at least a portion 308 of the enclosing wall 318 that is elastic include an elasticity that damps a pressure pulse from the infusion pump 216. The infusion pump 216, as shown in FIG. 2, is fluidly coupled with the drip chamber 206B. It should be noted that the infusion pump 216 used with embodiments is an infusion pump that is commonly known in the art to be used with IV therapy.

In one embodiment, the drip forming orifice 212 includes a flow resistance channel 324. The flow resistance channel 324 provides a hydraulic resistance to a fluid flowing from the outlet 316 to the inlet 302. The term, "hydraulic resistance", refers to the resistance to the movement of fluid through an area. For example, the flow resistance channel 324 resists the movement of fluid through the drip forming orifice 212 from the infusion pump 216 side. This hydraulic resistance interacts with the pressure damping elastic component (the air holding portion 310 and the portion 308 of the enclosing wall 318 that is elastic) to form a "damper" which attenuates pressure pulses originating downstream in the second fluid line 224 due to the infusion pump's 216 intake flow through a restriction in the second fluid line 224. Thus, the air holding portion 310 and the portion 308 of the enclosing wall 318 that is elastic (i.e., the pressure damping elastic component described herein) contribute additively to the total compliance of the drip chamber. That compliance, in turn, interacts with the flow resistance channel 324 to form what is called the 'damping' effect.

In one embodiment, the drip chamber 206B includes a pressure damper that shields the check valve 210 from a negative transient pressure. The negative transient pressure is that pressure caused by the pulsating pump, thereby drawing fluid towards the infusion pump 216 through any resistance in the fluid pathway (e.g., Secondary fluid pathway). If the check valve 210 were to receive the full effects of the pressure caused by the infusion pump 216 that is pulsating, the check valve 210 would open transiently, thereby allowing bursts of fluid to rapidly drip through the drip forming orifice 212 and ultimately through the drip chamber 206B.

The pressure damper includes the combination of the flow resistance channel 324 and the pressure damping elastic component described herein. The net damping effect, as measured by the highest frequency which is passed without attenuation, is inversely proportional to the product of the resistance and the compliance of the pressure damping elastic component (including the air holding portion 310 and the at least a portion 308 of the enclosing wall 318 having an elasticity). Thus, it is the two aspects working together that result in the effective damping of unwanted pressure waves. Additionally, aggressively increasing at least one of the following serves to attenuate pulses that originate in the infusion pump flow passing through the restriction of the Secondary pathway: the resistance to the movement of fluid through an area; and the compliance of the air holding portion 310 and the enclosing wall 318 having an elasticity.

Therefore, the damping provided by the flow resistance channel 324 together with the pressure damping elastic component, including elastic elements therein, protects the check valve 210 from exposure to negative-going transient pressure which could cause the check valve 210 to temporarily and prematurely open. This premature and intermittent opening may cause the unintended partial flow of the first fluid 234 while the second fluid 236 remains to be delivered.

Under some circumstances, there may be excess fluid in a drip chamber. This reduces both the ability of the clinician to visualize drops for monitoring, as well as reduces the elasticity, described above, that is useful in damping unwanted pressure waves. In one embodiment, the check valve 210 of the drip chamber 206B includes a bypass mechanism 326. The bypass mechanism 326 opens the check valve 210 in response to receiving an opening trigger, thereby releasing a fluid flowing in the first direction 320 through the check valve 210 from the outlet 316 to the inlet 302. In one embodiment, the opening trigger is a threshold pressure of the fluid flowing in the first direction 320 from the outlet 316 to the inlet 302. The threshold pressure refers to that pressure which is needed to cause a portion of the check valve 210 to open to let the fluid flow through. In one embodiment, the threshold pressure needed would be between 4 and 8 psi. For example, the threshold pressure may be provided by the nurse's fingers squeezing the body of the first drip chamber 206A to remove excess fluid out of the first drip chamber 206A and restore the normal amount of air. Of note, the first drip chamber 206A and bag must be inverted so that when the wall of the first drip chamber 206A is released from squeezing, it will draw air, and not fluid, from the bag.

In another embodiment, the opening trigger is a threshold force applied against the check valve 210, thereby causing the check valve 210 to deform from a first shape to a second shape. For example, a practitioner may deform the housing or activate an attached element that would trigger the bypass mechanism 326 to cause the check valve 210 to open to allow the fluid to flow there through. In one embodiment, the bypass mechanism 326 is a deformation characteristic of a component within the check valve 210 that changes shape, such as the shape of a bell curve that faces one direction to the shape of a bell curve that faces an opposite direction. The shape change leaves an opening within the interior flow passage 328 that allows for fluid to flow there through.

With reference to FIG. 4, an example drip chamber 206C is shown, including: a check valve 210 coupled with and between a spike 208 and a drip forming orifice 212. The spike 208 includes at least a portion of the interior flow passage 328 and an air passageway 412. In another embodiment, the spike 208 includes the interior flow passage 328 without the air passageway 412. For example, a drip chamber may not have a vent path, such as with bags whose walls collapse as the fluid is withdrawn, thus not requiring a path for replacement air to enter. The inlet 302 is at one end of the interior flow passage 328. An enlarged view 410 of the check valve 210 is also shown. It can be seen that the fluid flows through the portion of the interior flow passage 328 of the check valve 210, thereby flowing around an obstruction 408 in the middle of the check valve 210. It should be noted that a check valve that is known in the art may be used as part of some embodiments described herein. In one embodiment, the check valve includes the bypass mechanism 326, as described herein.

FIG. 4 also shows a drip forming orifice 212, along with a drip 402 of fluid falling from an end of the drip forming orifice 212. Further, the enclosing wall 318 couples with the first and second end, 312 and 314, respectively, of the drip chamber 206C, and houses within the spike 208, check valve 210 and drip forming orifice 212. Also shown is the pressure damping elastic component 406 that includes the air holding portion 310 and at least the portion 308 of the enclosing wall 318 that includes an elasticity. The fluid drips into the air holding portion 310 to form a volume of fluid 404. A portion of that volume of fluid 404 may then continue moving through components (such as the first fluid line 214, the infusion pump 216 and the patient IV fluid line 218) coupled with the drip chamber 206C to reach the patient.

With reference now to FIGS. 3 and 4, a device for managing fluid flow may be described, according to one embodiment. The device includes: a drip chamber 206B. The drip chamber 206B of the device includes, in one embodiment: an inlet 302; an outlet 316; and a check valve 210 positioned between the inlet 302 and the outlet 316. The check valve 210 manages fluid flowing between the inlet 302 and the outlet 316. In one embodiment, the drip chamber 206B further includes the flow resistance channel 324.

The example device further includes, in one embodiment, the enclosing wall 318 that couples the first end 312 with the second end 314. The enclosing wall 318 houses within at least the spike 208, the check valve 210 and the drip forming orifice 212. An additional embodiment of the device includes the pressure damping elastic component described herein. In yet another example embodiment, the device includes the pressure damper described herein.

In one example device, the check valve is the one-way check valve described herein. Further, in yet another embodiment, the one-way check valve includes the bypass mechanism described herein.

FIG. 5 is a flow diagram of an example method 500 for managing a flow of fluid within a flow control system, in accordance with embodiments.

Referring now to FIGS. 2-5, at 505 and as described herein, in one embodiment, the method 500 includes receiving 505 a fluid flow, the receiving occurring at a drip forming orifice 212 of a drip chamber 206C. The fluid flow occurs at a first rate in a first direction 320. At 510 and as described herein, in one embodiment, the drip forming orifice 212 resists the fluid flow. At 515 and as described herein, in one embodiment, the check valve 210 stops the fluid flow. The check valve 210 is coupled with and positioned between the spike 208 and the drip forming orifice 212. The spike 208 is integrally coupled with the first end 312 of the drip chamber 206C.

At 520 and as described herein, in one embodiment at least a portion 308 of an effect of a pressure pulse formed by the infusion pump 216 is damped. The infusion pump 216 is fluidly coupled with the drip chamber 206C. The damping 520 includes at least one of: in response to receiving the pressure pulse from the infusion pump 216, elastically expanding an air holding portion 310 and at least a portion 308 of the enclosing wall 318 of the drip chamber 206C; and in response to receiving the pressure pulses from the infusion pump 216, providing a hydraulic resistance to the fluid flow from an outlet of a second end of the drip chamber 206C to an inlet of a first end of the drip chamber 206C. Of note and as described herein, in one embodiment, the damping is produced not just by the pressure damping elastic component 406 and not just by the flow resistance channel 324, but rather by the combined effect of the pressure damping elastic component 406 and the flow resistance channel 324.

At 525 and as described herein, in one embodiment at least a portion 308 of an effect of a pressure pulse formed by the infusion pump 216 is damped. The infusion pump 216 is fluidly coupled with the drip chamber 206C via a tubing. The tubing elastically expands in response to the receiving of the pressure pulse from the infusion pump and provides a resistance within to the movement of the fluid there through.

At 530 and as described herein, in one embodiment a volume of fluid 404 that is stopped at the check valve 210 is released. The releasing of this volume of fluid 404 includes: receiving a check valve opening trigger; and in response to the receiving of the check valve opening trigger, opening the check valve 210. In one embodiment, the receiving of the check valve opening trigger includes the receiving of a threshold pressure that is applied by a fluid flowing in a first direction 320. In another embodiment, the receiving of the check valve opening trigger includes the receiving of a threshold force applied against the check valve 210, wherein the threshold force applied against the check valve 210 deforms the check valve 210 from a first shape to a second shape.

Figure 6:
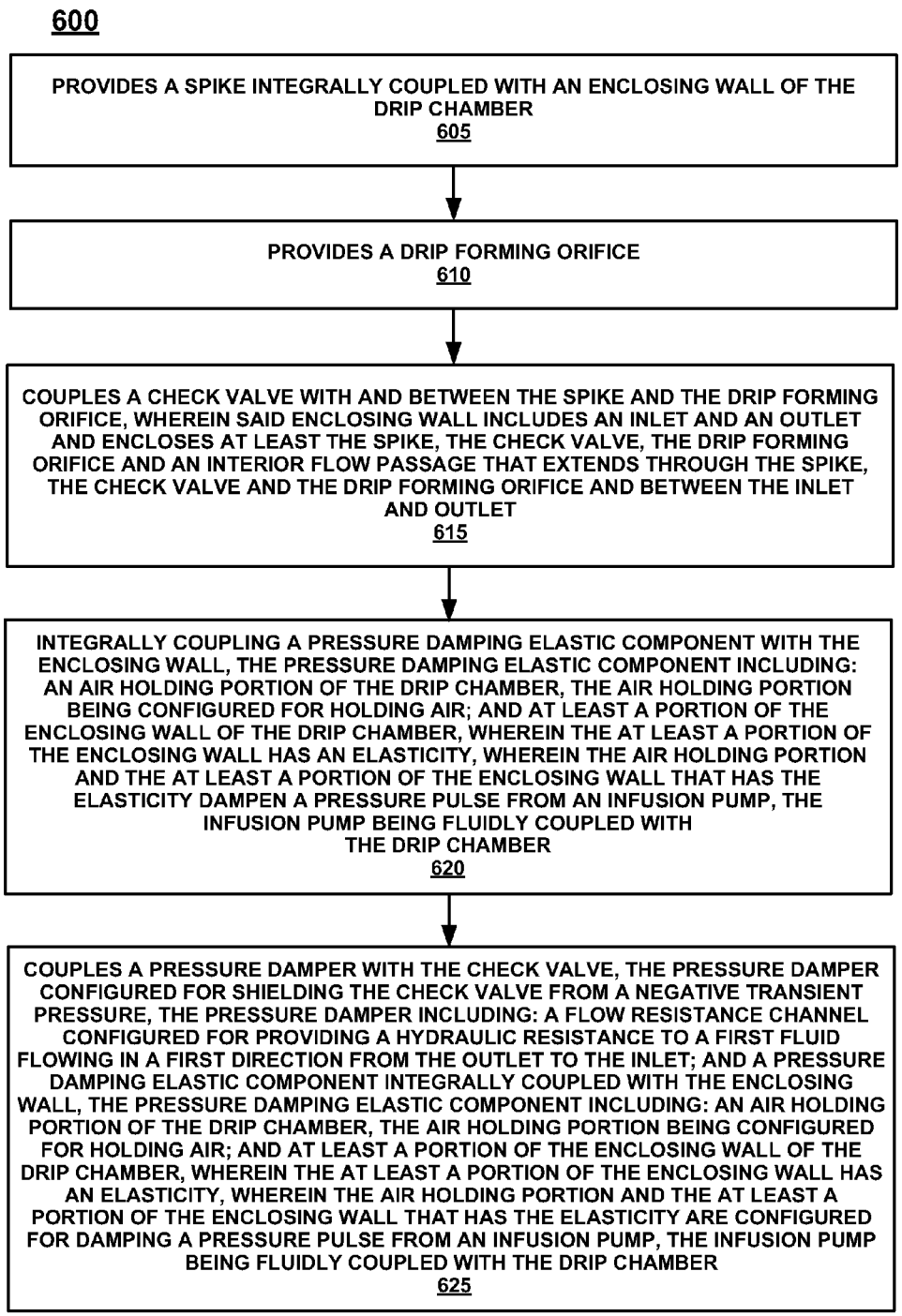
FIG. 6 shows a flow diagram of an example method for manufacturing a drip chamber, in accordance with an embodiment.

FIG. 6 is a flow diagram of a method 600 for manufacturing a drip chamber, such as drip chamber 206C of FIG. 4, in accordance with an embodiment.

Referring now to FIGS. 2-4 and 6, at 605 and as described herein, in one embodiment, the method 600 includes providing 605 a spike 208 integrally coupled with an enclosing wall 318 of the drip chamber 206C. At 610 and as described herein, in one embodiment, the drip forming orifice 212 is provided. At 615 and as described herein, in one embodiment, the check valve 210 is coupled with and between the spike 208 and the drip forming orifice 212. In one embodiment and as described herein, the check valve 210 is a one-way check valve. In another embodiment and as described herein, the check valve 210 includes the bypass mechanism 326.

Further, and as described herein, in one embodiment, the enclosing wall 318 is integrally coupled with the spike 208. The enclosing wall 318 includes an inlet 302 and an outlet 316 and encloses at least the spike 208, the check valve 210, the drip forming orifice 212 and the interior flow passage 328 (that extends through the spike 208, the check valve 210 and the drip forming orifice 212 as well as between the inlet 302 and the outlet 316).

At 620 and as described herein, in one embodiment, the pressure damping elastic component 406 is integrally coupled with the enclosing wall 318. The pressure damping elastic component 406 includes the air holding portion 310 of the drip chamber 206C and at least a portion of the enclosing wall 318 of the drip chamber 206C that is elastic, as is described herein.

At 625 and as described herein, in one embodiment, the check valve 210 is coupled with the pressure damper. The pressure damper shields the check valve 210 from a negative transient pressure. The pressure damper includes: the flow resistance channel 324 and the pressure damping elastic component 406 that is described herein.

Section Two

Vacuum Activated Catch for Managing a Fluid Flow

Herein, various embodiments of a device for controlling fluid flow, a flow control system and a method of manufacturing the device are described. The description begins with a continuation of the brief general discussion, in Section One regarding the example Drip Chamber above, of the traditional flow control system and methods for delivery of Secondary medications. This general discussion provides a framework of understanding for more particularized descriptions of features and concepts of operation associated with one or more embodiments of the described device and flow control system.

Flow Control Systems with Respect to Managing Fluid Flow

Referring to FIG. 1, traditional methods for delivery of Secondary medications include employing the check valve 116 in the Primary set while lowering the Primary container 104 with a hanger 102 to create a back pressure against the check valve 116, thus keeping it closed until the Secondary fluid 134 has been delivered. This requires, but does not always achieve, a very low flow resistance in the Secondary pathway. When high flow rates are involved and/or the resistance of the Secondary pathway is not sufficiently low, or when there is insufficient elevation difference between the Primary and Secondary fluids, 106 and 134, respectively, some Primary fluid 106 will flow when only the Secondary fluid 134 is intended to flow. This condition is referred to as "sympathetic flow". This results in the delayed completion of the Secondary fluid 134. In other words, the pressure lost through excess resistance in the Secondary pathway effectively reduces the pressure differential across the check valve 116. This allows intermittent flow of the Primary fluid 106 to occur even though there may still be significant fluid left in the Secondary container 136.

The traditional use of the check valve together with elevation differential has the following inherent weaknesses: it requires the manual lowering of the Primary container 104; uncertainty exists for the operator regarding the needed elevation with regards to lowering the Primary container 104; the resistance to the flow in the Secondary fluid line 128 may vary from setup to setup and may cause unintended flow from the Primary container 104, thereby delaying the completion of the delivery of the Secondary fluid 134; air may be entrained when the Primary container 104 is lowered below the Primary port entrance; and Primary infusion setups used bear the cost of manufacturing the check valve 116, even though only a small percentage of the Primary infusion setups are used for Secondary delivery of medication (and thus use the check valve 116).

In accordance with various embodiments, an example flow control system includes a device for controlling fluid flow and a sealable component which automatically stops flow once fluid in the container is depleted (such as, but not limited to, a ball float valve) positioned within a drip chamber. The device includes a tubing clamp coupled with a vacuum activated catch. When the tubing clamp is secured in a closed position by the vacuum activated catch, a Primary fluid line is pinched closed. When the vacuum activated catch releases the tubing clamp to an open position, the first fluid line is also released into an open position. The vacuum activated catch is also coupled with the Secondary container via a Secondary fluid line. In between the Secondary container and the vacuum activated catch is a check valve. This check valve prevents reverse flow into the Secondary container when the tubing clamp is open.

Further, in embodiments, there is no need for the Primary container to be lowered, which simplifies the work of a caregiver, thus removing a significant source of error.

The sealable component is coupled with the Secondary container and stops the flow of the Secondary fluid when the Secondary container empties to the drip chamber. When the sealable component seals shut, thereby closing an interior flow passage within the drip chamber, the pump's intake draws a vacuum in the Secondary fluid pathway. This vacuum deforms a membrane in the vacuum activated catch that is coupled with the Secondary fluid line, which then releases and opens the tubing clamp, thereby opening the Primary fluid line and allowing the Primary fluid flow to commence there through.

Embodiments eliminate the need for a costly check valve to be placed in every Primary infusion setup. Further, embodiments help to ensure on-time Secondary delivery of fluids. Moreover, the need for a hanger and/or to reposition containers is removed. Additionally, the device may other forms of "vacuum activated" clamps or valves, such as, but not limited to, using a lever arm to minimize the force needed to lock and release the clamping of a Primary fluid line.

The following discussion will focus on example structures and operations of embodiments.

Figure 7:
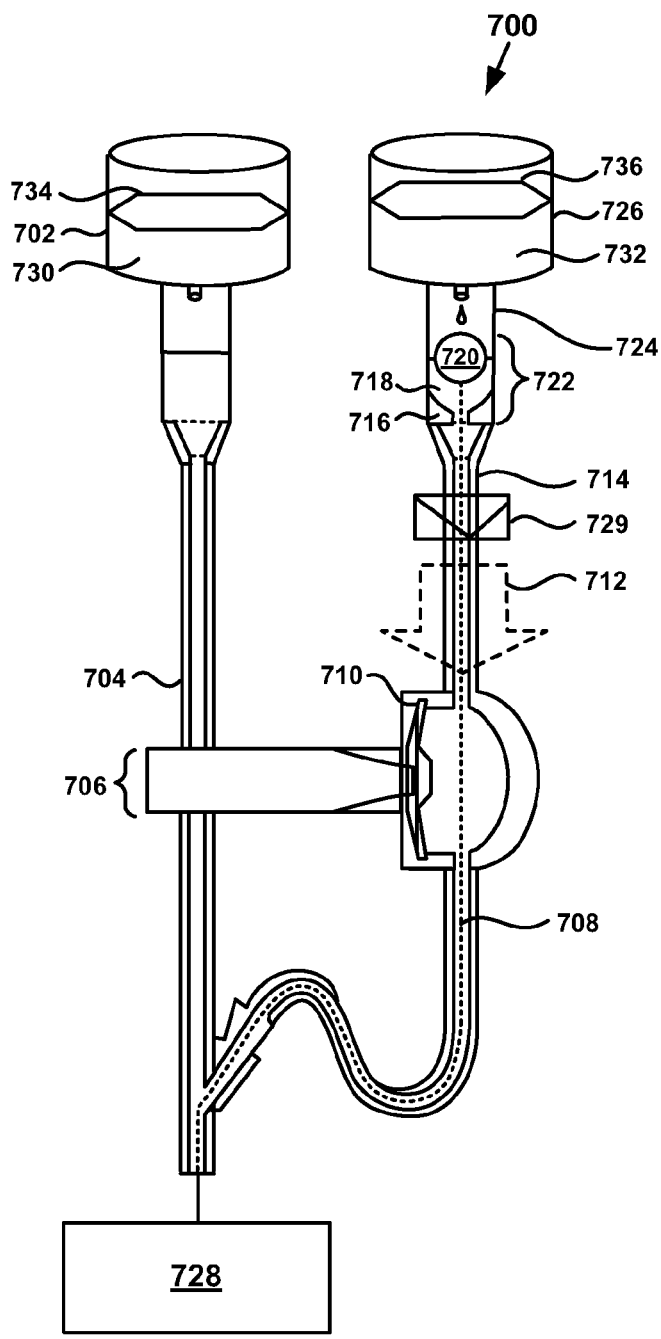
FIG. 7 shows an example flow control system, in accordance with an embodiment.

FIG. 7 shows a tubing clamp 706 coupled with a vacuum activated catch 710, within a flow control system 700, in accordance with an embodiment. In embodiments, the flow control system 700 includes: a tubing clamp 706; a vacuum activated catch 710 retainably coupled with the tubing clamp 706 and a second fluid line 714; a second drip chamber 724 coupled with and between the second container 726 and the second fluid line 714; and an infusion pump 728 coupled with the first and second fluid lines, 704 and 714, respectively. Additionally, in one embodiment, a one-way check valve 729 is shown in the second tubing pathway. This one-way check valve 729 prevents flow from the first container 702 when the tubing clamp 706 is open. In one embodiment, the one-way check valve 729 is incorporated within the design of the device 800A/800B (of FIGS. 8A and 8B, respectively), which includes the tubing clamp 706 and the vacuum activated catch 710. In another embodiment, the one-way check valve 729 is a conventional component positioned separately from the device 800A/800B.

In one embodiment, the first container 702 is a Primary container, the first fluid line 704 is a Primary fluid line, the first fluid 730 is a Primary fluid, the second container 726 is a Secondary container, the second drip chamber 724 is a Secondary drip chamber, the second fluid line 714 is a Secondary fluid line, the second fluid 732 is a Secondary fluid, the first fluid level 734 is a Primary fluid level, the second fluid level 736 is a Secondary fluid level, the first fluid flow is a Primary fluid flow, and the second fluid flow is a Secondary fluid flow. Thus, the descriptions herein, with regards to FIGS. 7-10, using the terms "first" and "second" may be associated with the delivery of Secondary medications, in one embodiment.

Figure 8A:
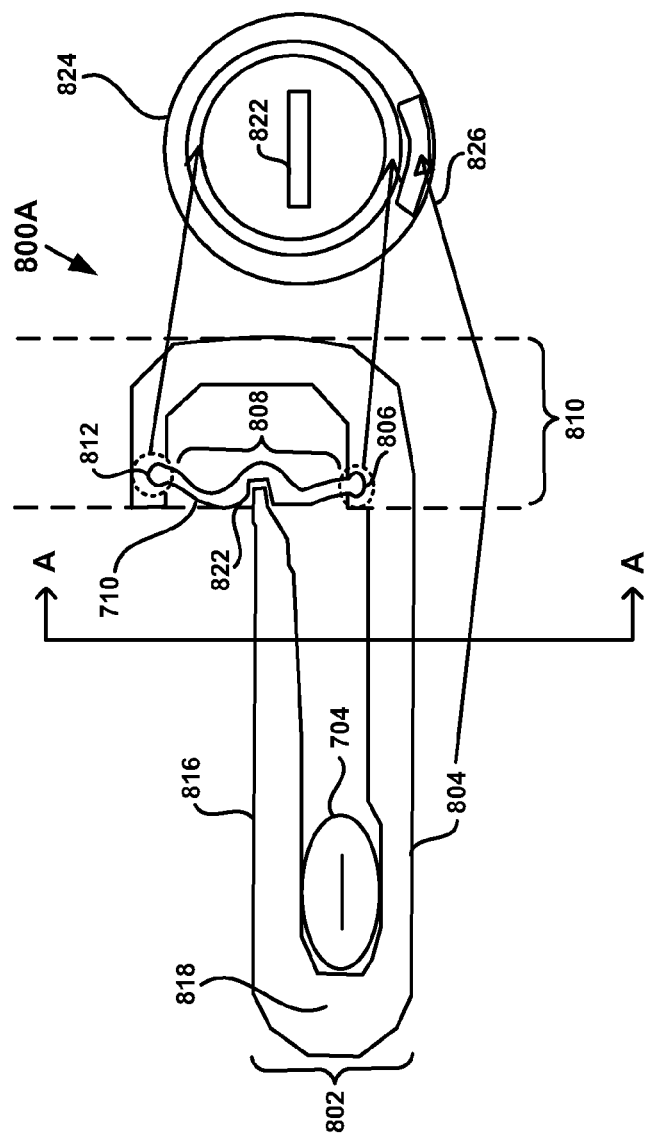
FIG. 8A shows an example device, a tubing clamp coupled with a vacuum activated catch, the tubing clamp being in the closed position, in accordance with an embodiment.

FIG. 8A shows a device 800A, including a tubing clamp 706 (of FIG. 2) coupled with a vacuum activated catch 710. Referring to FIGS. 7 and 8A, in one embodiment, the tubing clamp 706 includes a first arm 816 and a second arm 804 that is coupled with the first arm 816 via a connector 818. In one embodiment, the connector 818 is flexible. Thus, in one embodiment, the connector 818 and the first arm 816 and second arm 804 to which it is attached are made of one piece. In another embodiment, the combination of the first arm 816 and the second arm 804 to which it is attached is made of at least two pieces that are manufactured to appear to be a single piece. In yet another embodiment, the connector 818 to which the first arm 816 and the second arm 804 is attached is a hinge-like component such that portions of the hinge-like component open and close, thereby opening and closing the first arm 816 and the second arm 804. In one example, connector 818 is an axle about which first arm 816 and second arm 804 of the tubing clamp 706 pivot. Further, in one embodiment, a spring is used to assure that when the tubing clamp 706 is opened, and the first arm 816 and the second arm 804 swing away. In another embodiment, the wall itself of the tubing clamp 706 provides sufficient force to cause a desired opening of the first arm 816 and the second arm 804.

Further, in one embodiment, the second arm 804 is attached to a hooked end 810. For example, in one embodiment, the second arm 804 and the hooked end 810 are a single piece. However, in another embodiment, the combination of the second arm 804 and the hooked end 810 to which the second arm 804 is attached is made of at least two pieces that are manufactured to appear to be a single piece. Of note, it should be appreciated that the first arm 816, the clamping mechanism 802, the second arm 804 and the hooked end 810 may be a single piece or multiple pieces attached to each other, or any combination thereof.

Moreover, the first arm 816 and the second arm 804, in one embodiment, are long, slender beams. However, it should be appreciated that the shape and length of the first arm 816 and the second arm 804 may be any shape and length such that the first arm 816 articulates with the holding notch 822 of the vacuum activated catch 710, thereby holding it in place.

Additionally and as will be discussed below in more detail, a first attachment portion 812 and a second attachment portion 806 of the vacuum activated catch 710 are coupled with the hook end 810 of the tubing clamp 706 such that a portion of the first arm of the tubing clamp 706 may be held in place by one or more notches (such as but not limited to holding notch 822) in the vacuum activated catch 710. Of note, FIG. 8A also shows section AA, an end view of a circular shaped deformable element 824, which is one example of a vacuum activated catch 710. As seen, the circular shaped deformable element 824 includes the holding notch 822. The arrow pointing from the first attachment portion 812 to the circular shaped deformable element 824 shows an attachment point at 826. This represents where the first attachment portion 812 attaches to the vacuum activated catch 710.

Referring still to FIGS. 7 and 8A, the tubing clamp 706 includes the clamping mechanism 802 that holds closed the first fluid line 704 while a second fluid 732 flows along the second fluid line 714 from the second container 726. The first fluid line 704 delivers a flow of a first fluid. The direction 712 of the flow of the second fluid 732 is from the second container 726 towards the infusion pump 728. The tubing clamp 706 is in the closed position, in accordance with an embodiment.

The second drip chamber 724 includes a sealable component 722 that seals closed an interior flow passage 708 within the second drip chamber 724 when the second container 726 is empty (or nearly empty [i.e. substantially empty]), thereby obstructing the flow of the second fluid 732. In one embodiment, the sealable component 722 is a ball float valve. The ball float valve includes a ball 720 and a base 716, wherein when the second container 726 is empty (or nearly empty [i.e. substantially empty]), the ball 720 sets within the base 716, thereby sealing the interior flow passage 708 within the second drip chamber 724, such that the ball 720 prevents whatever small amounts of fluid that are left, if any, within the second drip chamber 724 and/or the second container 726 from flowing through to the second fluid line 714. Of note, there can be some fluid left in the second container 726 since some bags (e.g., second container 726) have 'side lobes' where fluid may sequester and thus not flow into the spike, the drip orifice, and finally the drip chamber (e.g., second drip chamber 724). However, the activation of the 'sealable' element occurs when no further fluid is entering the second drip chamber 724 while the pump draws fluid out of it. This is true whether the 'ball float' design, the filter, or any other are employed.

For example and referring to FIG. 7, after the spike of the second drip chamber 724 is placed in the second container 726, fluid flows into the second drip chamber 724. The ball 720 has buoyancy that causes it to float on the volume of fluid 718 that fills a portion of the second drip chamber 724. When the second container 726 is emptied (or nearly empty [i.e. substantially empty]) and all (or nearly all) of the fluid has exited the second drip chamber 724 through the interior flow passage 708 into the second fluid line 714, the ball 720 sets into the base 716, thus sealing the portion of the interior flow passage 708 within the second drip chamber 724.

Figure 9:
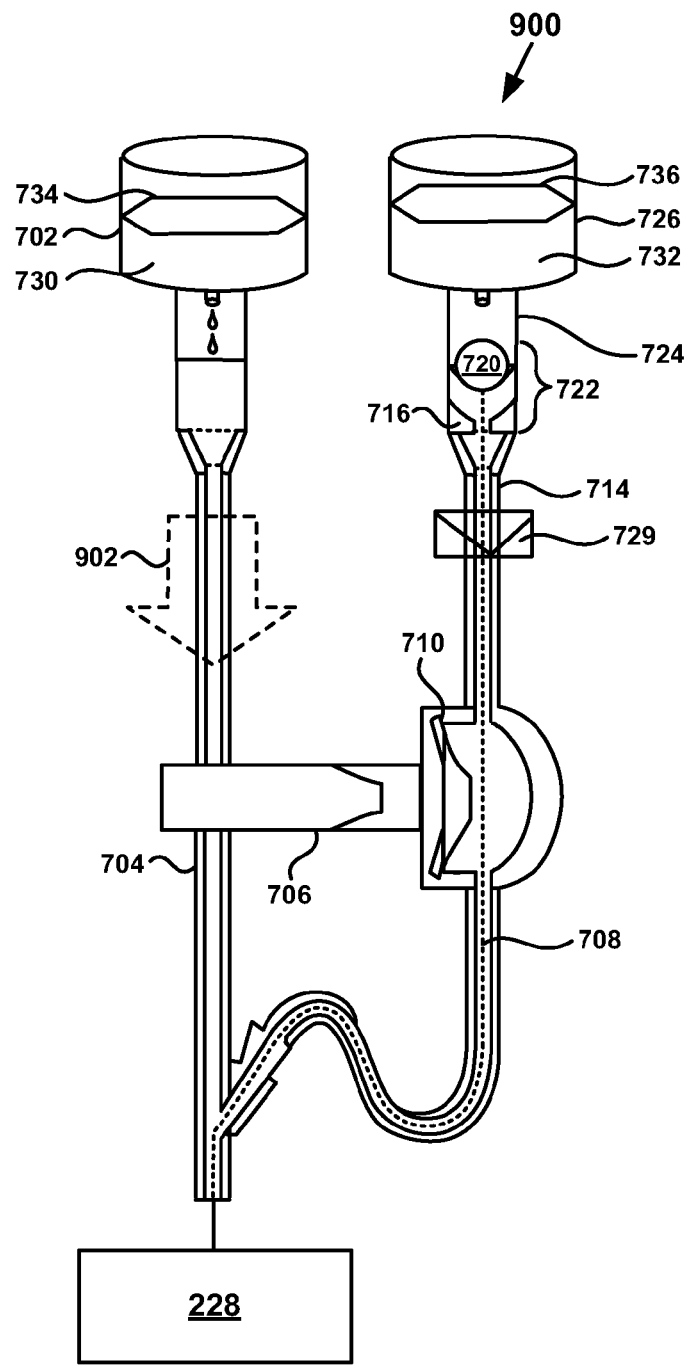
FIG. 9 shows an example flow control system, in accordance with an embodiment.

FIG. 9 shows a tubing clamp 706 coupled with a vacuum activated catch 710, within a flow control system 900, in accordance with an embodiment. FIG. 9 also shows the ball 720 set into the base 716, as a result of the second container 726 being empty (or nearly empty [i.e. substantially empty]), and/or the infusion pump 728 drawing a vacuum through the second fluid line 714, thus pulling the ball 720 into the base 716.

Figure 8B:
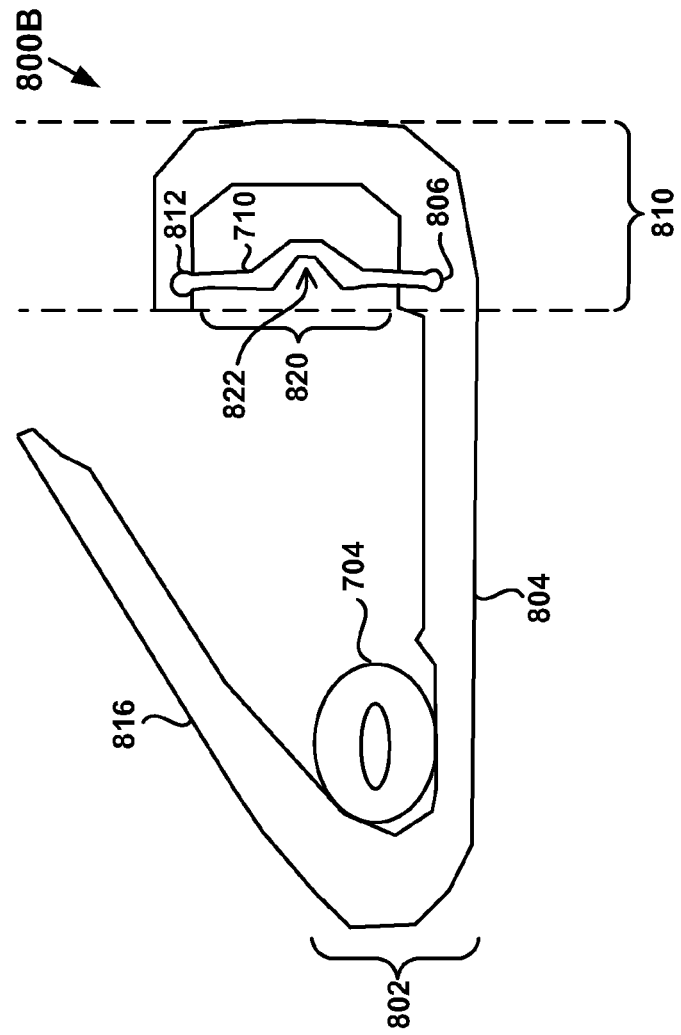
FIG. 8B shows an example device, a tubing clamp coupled with a vacuum activated catch, the tubing clamp being in the open position, in accordance with an embodiment.

Of note, the interior flow passage 708 is shown, in both FIGS. 7 and 9, as a dotted line from and through the second drip chamber 724 and the second fluid line 714. When the second container 726 is emptied (or nearly emptied), there is no longer any fluid and/or enough fluid to support a floating ball 720 such that the interior flow passage 708 is kept open. The ball 720 then sets in the base 716. The infusion pump 728, in operation, draws a vacuum within the second fluid line 714 and away from the second drip chamber 724. The displacement of the fluid by the pump creates a negative pressure within the second fluid line 714, resulting in the deformation of the vacuum activated catch 710. For example, the vacuum activated catch 710 may pop inwards, releasing the first attachment portion 812, as shown in FIGS. 8B and 9, in response to the negative transient pressure. Since the vacuum activated catch 710 is constructed of a movable element, the vacuum activated catch 710 has the ability to change shapes when receiving a pressure that overcomes the material's inherent characteristics causing stiffness. The inward deformation will cause a portion of the tubing clamp 706 to be released, as will be explained herein. The movable element may be, but is not limited to, any of the following: a deformable membrane; a piston; a rolling hat seal; and any structure capable of being displaced by the vacuum established by the closure of the second fluid path and continued intake of fluid by the infusion pump 728.

In another embodiment, the sealable component 722 is a filter (not shown in the Figures). For example, but not limited to such, in one embodiment the filter has a diameter of 0.22 micron. The filter is placed in the base of the second drip chamber 724. When air is on one side and fluid is on the other side of the filter, a meniscus, having a bubble point pressure, is created. The bubble point pressure blocks air from flowing through the filter. The bubble point pressure increases in inverse proportion to the filter's diaphragm diameter. In other words, the filter produces a bubble point pressure that is sufficient to activate the movable element, thereby releasing the vacuum activated catch 710 that is closing the first tubing.

FIG. 8B shows a device 800B, the tubing clamp 706 (of FIG. 7) coupled with the vacuum activated catch 710. The tubing clamp 706 is in an open position, in accordance with an embodiment. Referring now to FIGS. 8A and 8B, the vacuum activated catch 710 includes a movable element that is coupled with the tubing clamp 706. The movable element changes from a first shape 808 to a second shape 820 upon receipt of a deforming vacuum pressure. When the movable element is in the first shape 808, the vacuum activated catch 710 retains the tubing clamp 706 in a closed position. When the movable element is in the second shape 820, the vacuum activated catch 710 releases the tubing clamp 706 into an open position, thereby allowing the flow of the first fluid 730 to commence within the first fluid line 704.

In one embodiment, and as described herein, a portion of the first arm 816 of the tubing clamp 706 is releasably secured by the holding notch 822 of the vacuum activated catch 710. (Again, it should be noted that the vacuum activated catch 710 may include more than one holding notch 822.) For example, in one embodiment, the movable element has a holding notch 822 for holding the first arm 816 of the tubing clamp 706 in place. In one embodiment, the movable element is of a shape that is capable of changing from a first shape 808 to a second shape 820 (of FIG. 8B) upon applied vacuum (a positive pressure) and/or force such that the first arm 816 of the tubing clamp 706 is released from the holding notch 822 of the vacuum activated catch 710, such as, but not limited to, a cup shape, a disk shape, or a combination thereof.

Referring to FIG. 8A, it can be seen that in one embodiment, when the movable element of the vacuum activated catch 710 is in a first shape 808, the vacuum activated catch 710 secures closed the first arm 816 of the tubing clamp 706 such that the first fluid line 704 is pinched closed.

Referring now to FIG. 8B, the tubing clamp 706 is in an open position. In one embodiment, the movable element of the vacuum activated catch 710 releases the first arm 816 of the tubing clamp 706 while the movable element is in the second shape 820, such that the first fluid line 704 opens. It should be appreciated that the second shape 820 of the movable element may be any shape that allows the first arm 816 to be released from its secured position such that the first fluid line 704 is then opened. The second shape 820 may be that shape which is different from the first shape 808, such that the end of the first arm 816 can no longer be secured in a closed position. For example, but not limited to such, if the first shape is a bell curve, then the second shape 820 may be flat.

The infusion pump 728 draws a vacuum in the second fluid line 714, thereby creating the deforming force (the pressure is a negative value) when the second container 726 is substantially empty (i.e. empty or nearly empty). In one embodiment, the deforming pressure is a negative pressure caused by the drawing of the vacuum. More specifically, the infusion pump 728 withdraws fluid from the blocked tubing, thereby drawing or producing a vacuum. In one embodiment, the infusion pump 728 has a pressure sensor.

Further, as can be seen, once the movable element pops in and releases the first arm 816 of the tubing clamp 706, thus opening the first fluid line 704, the first fluid 730 commences flowing in the direction 902 from the first container 702 towards the infusion pump 728. Since the first fluid level 734 is now higher than fluid in the second container 726, the one-way check valve 729 is forced closed so that only the fluid from the first container 702 flows only to the infusion pump 728.

With reference to FIGS. 7-9, an embodiment of a device may be described. In one embodiment, a device includes a tubing clamp 706 and a vacuum activated catch 710. The tubing clamp 706, according to one embodiment, holds closed the first fluid line 704 while the second fluid 732 flows along a second fluid line 714 from the second container 726, wherein the first fluid line 704 delivers a flow of first fluid 730. The vacuum activated catch 710, according to one embodiment, is coupled with the second fluid line 714 and is releasably secured as described herein, by the tubing clamp 706. The term, "releasably secured", refers to the ability of the tubing clamp 706 to release, as well as hold in place, a portion of the vacuum activated catch 710. Upon receipt of a deforming force, the catch 710 opens and allows the flow of the first fluid 730 within the first fluid line 704. In one embodiment, the deforming force is due to a vacuum caused by the infusion pump 728 that is coupled with the second fluid line 714, wherein the infusion pump 728 draws a vacuum during operation by aspirating fluid from the tubing.

In one embodiment, the tubing clamp 706 includes the clamping mechanism 802 described herein. In yet another embodiment, the vacuum activated catch 706 includes the movable element described herein.

A further embodiment of the tubing clamp 706 of the example device includes a first arm 816 and a second arm 804 coupled with the first arm 816 via the connector 818, wherein the connector 818 is flexible.

FIG. 10 is a flow diagram of an example method 1000 for manufacturing a device, in accordance with embodiments.

Referring now to FIGS. 7-10, at 1005 and as described herein, in one embodiment, the method 1000 includes providing a tubing clamp 706, wherein the tubing clamp 706 includes a clamping mechanism 802 configured for holding closed a first fluid line 704 while the second fluid 732 flows along a second fluid line 714 from a second container 726. The first fluid line 704 delivers a flow of a first fluid 730. Further, in one embodiment, the providing 1005 of the tubing clamp 706 includes providing a first arm 816 and a second arm 804 of the tubing clamp 706, and coupling the first arm 816 and the second arm 804 with the connector 818, wherein the connector 818 is flexible.

At 1010 and as described herein, in one embodiment the method 1000 includes coupling a vacuum activated catch 710 with the tubing clamp 706, wherein the vacuum activated catch 710 includes a movable element coupled with the tubing clamp 706 and configured for changing from a first shape 808 to a second shape 820 upon receipt of a deforming force. When the movable element is in the first shape 808, the vacuum activated catch 710 retains the tubing clamp 706 in a closed position. When the movable element is in the second shape 820, the vacuum activated catch 710 releases the tubing clamp 706 into an open position, thereby allowing the flow of the first fluid 730 to commence within the first fluid line 704. Further, in one embodiment, the coupling 1010 of the vacuum activated catch 710 includes coupling a first attachment portion 812 and a second attachment portion 806 of the movable element with a hooked end 810 of the second arm 804 of the tubing clamp 706.

At 1015 and as described herein, in one embodiment the method 1000 includes disposing at least one latching element on the movable element, such that the movable element is enabled to secure the tubing clamp 706 in a closed position. For example and with reference to FIG. 8A, the first shape 808 includes a concave portion that receives an end of the first arm 816. The fitting together of the concave portion and the end of the first arm 816 shows the function of the at least one latching element of the first shape 808, that of the concave portion. In other words, areas may be disposed on the movable element that are capable of receiving one or more portions of the first arm 816 such that the movable element secures and retains the first arm 816 in a position that allows the first fluid line 704 to be and remain pinched closed, until released.

Further, the vacuum activated catch 710 functions in a bi-stable mode. That is, once it 'switches' to the released position, it no longer requires vacuum force to remain in that position. Thus, as soon as the clamp opens, the vacuum disappears. One embodiment provides a means for the operator to place the vacuum operated catch 710 back into the latching position. For example, but not limited to such example, a tab is used that enables the vacuum activated catch 710 to be manually pulled out and placed back into the latching position. In another embodiment, a pushing element from within the fluid path is used, the pushing element allowing the vacuum activated catch 710 to be placed back into the latching position.

Section Three

An Example Drip Chamber Integrated within an Example Flow Control System

Herein, various embodiments of a flow control system integrated with a drip chamber are described. The description below describes the integration of the example drip chamber discussed in Section One above with the example flow control system discussed in Section Two above.

Figure 11:
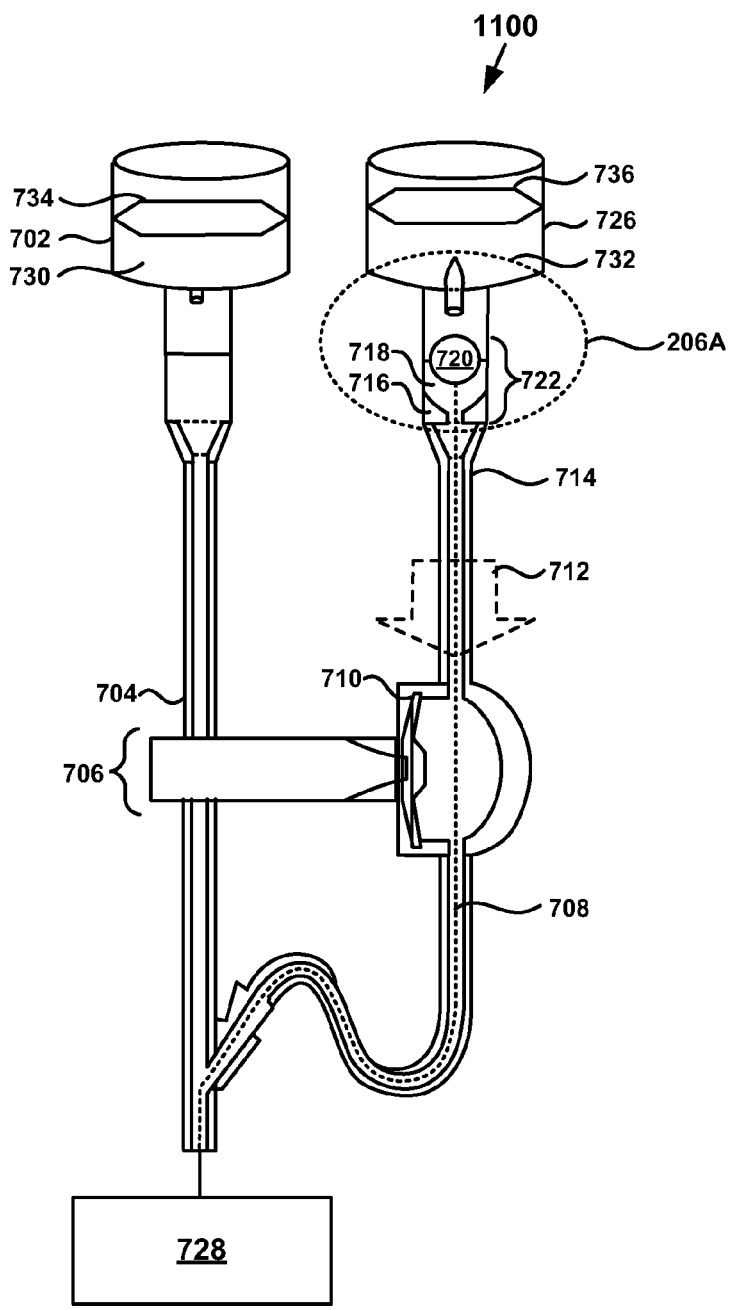
FIG. 11 shows a block diagram of an example flow control system, including an example drip chamber, in accordance with an embodiment.

FIG. 11 shows a tubing clamp 706 coupled with a vacuum activated catch 710, within a flow control system 1100, in accordance with an embodiment. In embodiments, the flow control system 1100 includes: the tubing clamp 706; the vacuum activated catch 710 retainably coupled with the tubing clamp 706 and the second fluid line 714; the first drip chamber 206A (of FIG. 2) coupled with and between the second container 726 and the second fluid line 714; and the infusion pump 728 coupled with the first and second fluid lines, 704 and 714, respectively. FIG. 11 further shows, in accordance with various embodiments: the first container 702

In one embodiment, the first container 702 is a Primary container, the first fluid line 704 is a Primary fluid line, the first fluid 730 is a Primary fluid, the second container 726 is a Secondary container, the first drip chamber 206A is a Secondary drip chamber, the second fluid line 714 is a Secondary fluid line, the second fluid 732 is a Secondary fluid, the first fluid level 734 is a Primary fluid level, the second fluid level 736 is a Secondary fluid level, the first fluid flow is a Primary fluid flow, and the second fluid flow is a Secondary fluid flow. Thus, the descriptions herein, with regards to FIGS. 7-11, using the terms "first" and "second" may be associated with the delivery of Secondary medications, in one embodiment.

In one embodiment and as described herein, the tubing clamp 706 includes the clamping mechanism 802 (of FIGS. 8A and 8B) that holds closed the first fluid line 704 while the second fluid 732 flows along the second fluid line 714 from the second container 726. The first fluid line 704 is coupled with the first container 702 and delivers a flow of the first fluid 730.

Referring to FIG. 3, the example drip chamber 206B (a cross-sectional view of the example first drip chamber 206A) includes in one embodiment and as described herein the following: the first end 312 having an inlet 302; the second end 314 having an outlet 316; a spike 208 integrally coupled with the first end 312; a drip forming orifice 212 coupled with the spike 208; a check valve 210 disposed between and coupled with the spike 208 and the drip forming orifice 212; the enclosing wall 318 coupling the first end 312 and the second end 314; and the sealable component 722 (of FIG. 7).

Referring now to FIGS. 3 and 11, in one embodiment and as described herein, the check valve 210 manages the fluid flowing between the inlet 302 and the outlet 316 through the interior flow passage 328 that extends at least through the spike 208. In one embodiment, the enclosing wall 318 houses within at least the spike 208, the check valve 210 and the drip forming orifice 212. In one embodiment and as described herein, the sealable component 722 (including the ball 720 and the base 716 that are intermittently separated by the volume of fluid 718; see FIGS. 7 and 9) seals closed the interior flow passage 328 within the drip chamber 206B when the second container 726 is substantially empty, thereby obstructing the flow of the second fluid 732.

The vacuum activated catch 710 includes a movable element coupled with the tubing clamp 706, according to one embodiment and as described herein. The movable element changes from a first shape (e.g., first shape 808 of FIG. 8A) to a second shape (e.g., second shape 820 of FIG. 8B) upon receipt of a deforming force, wherein when the movable element is in the first shape, the vacuum activated catch 710 retains the tubing clamp 706 in a closed position. When the movable element is in the second shape, the vacuum activated catch 710 releases the tubing clamp 706 in an open position, thereby allowing the flow of the first fluid 730 to commence within the first fluid line 704, according to one embodiment.

In another embodiment and as described herein, the infusion pump 728 draws a vacuum in the second fluid line 714, thereby creating the deforming force when the second container 726 is substantially empty.

The check valve 210 incorporated in the Secondary set prevents the reverse flow of the Primary fluid (i.e., first fluid 730) into the Secondary container (i.e., the second container 726). For example, the hydrostatic pressure of the fluid in the Primary fluid line will be greater than that in the Secondary fluid line at the moment the tubing clamp 706 opens on the Primary fluid line. Additionally, the check valve 210 facilitates keeping the ball 720 from moving away from the base 716 (and thus re-opening), thereby preventing the backward flow of the Primary fluid flow into an empty Secondary container (i.e., second container 726). While employing the sealable component 722 (including the ball 720 and base 716) and without the check valve's 210 presence, an amount of Primary fluid would flow backward into the Secondary container through the opened sealable component 722, while still another amount of Primary fluid would continue to flow to the infusion pump 728. However, this backflow into the Secondary container wouldn't be safe in cases such as chemo delivery. It would be unsafe for there to be any fluid in the Secondary container that once contained the chemo.

Thus, the advantages of integrating the example first drip chamber 206A (including the check valve 210) along the Secondary pathway together with the tubing clamp 706 and the vacuum activated catch 710 include at least saving costs, creating a safer environment and the simplicity of its design that renders significant benefits.

All statements herein reciting principles, aspects, and embodiments as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of embodiments, therefore, is not intended to be limited to the embodiments shown and described herein. Rather, the scope and spirit of embodiments are embodied by the appended claims.

What is claimed is:

1. A device comprising:
   a tubing clamp comprising:
      a clamping mechanism configured for holding closed a first fluid line while a second fluid flows along a second fluid line from a container, said first fluid line configured for delivering a flow of a first fluid;
      a first arm; and
      a second arm coupled with said first arm via a connector, wherein said connector is flexible; and
   a vacuum activated catch retainably coupled with said tubing clamp and coupled with said second fluid line, said vacuum activated catch comprising:
      a movable element coupled with said tubing clamp and configured for changing from a first shape to a second shape upon receipt of a deforming pressure, wherein when said movable element is in said first shape, said vacuum activated catch retains said tubing clamp in a closed position, and when said movable element is in said second shape, said vacuum activated catch releases said tubing clamp into an open position, thereby allowing said flow of said first fluid to commence within said first fluid line.

2. The device of claim 1, wherein said movable element is releasably secured by said tubing clamp.

3. The device of claim 1, wherein said movable element of said vacuum activated catch is configured for securing closed said first arm of said tubing clamp while said movable element is in said first shape.

4. The device of claim 1, wherein said movable element of said vacuum activated catch is configured for releasing said first arm of said tubing clamp while said movable element is in said second shape.

5. The device of claim 1, wherein said movable element comprises:
   a first attachment portion; and
   a second attachment portion, wherein said first attachment portion and said second attachment portion of said movable element are coupled with a hooked end of said second arm of said tubing clamp.

6. The device of claim 1, wherein said deforming pressure is a negative pressure caused by an infusion pump coupled with said second line, wherein said infusion pump draws a vacuum during operation.

7. A device comprising:
   a tubing clamp configured for holding closed a first fluid line while a second fluid flows along a second fluid line from a container, said first fluid line configured for delivering a flow of a first fluid, the tubing clamp comprising:
      a first arm; and
      a second arm coupled with said first arm via a connector, wherein said connector is flexible; and
   a vacuum activated catch releasably secured by said tubing clamp and coupled with said second fluid line, said vacuum activated catch configured for, upon receipt of a deforming pressure, opening and allowing flow of said first fluid within said first fluid line, wherein said vacuum activated catch comprises:
      a movable element coupled with said tubing clamp and configured for changing from a first shape to a second shape upon receipt of said deforming pressure, wherein when said movable element is in said first shape, said vacuum activated catch retains said tubing clamp in a closed position, and when said movable element is in said second shape, said vacuum activated catch releases said tubing clamp into an open position, thereby allowing said flow of said first fluid to commence within said first fluid line.

8. The device of claim 7, wherein said tubing clamp comprises: a clamping mechanism configured for holding closed said first fluid line while said second fluid flows along said second fluid line from said container.

9. The device of claim 7, wherein said movable element of said vacuum activated catch is configured for securing closed said first arm of said tubing clamp while said movable element is in said first shape.

10. The device of claim 7, wherein said movable element of said vacuum activated catch is configured for releasing said first arm of said tubing clamp while said movable element is in said second shape.

11. The device of claim 7, wherein said movable element comprises:
- a first attachment portion; and
- a second attachment portion, wherein said first attachment portion and said second attachment portion of said movable element are coupled with a hooked end of said second arm of said tubing clamp.

12. The device of claim 7, wherein said deforming pressure is a negative pressure caused by an infusion pump coupled with said second line, wherein said infusion pump draws a vacuum during operation.

* * * * *